United States Patent
Meth-Cohn et al.

(10) Patent No.: US 6,734,196 B2
(45) Date of Patent: May 11, 2004

(54) SUBSTITUTED PYRIDINE OR PIPERIDINE COMPOUNDS

(75) Inventors: Otto Meth-Cohn, Morpeth (GB); Chu-Yi Yu, Oxford (GB); Pierre Lestage, La Celle St Cloud (FR); Marie-Cécile Lebrun, Asnieres (FR); Daniel-Henri Caignard, Le Chesnay (FR); Pierre Renard, Le Chesnay (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 10/306,024

(22) Filed: Nov. 27, 2002

(65) Prior Publication Data

US 2003/0139408 A1 Jul. 24, 2003

Related U.S. Application Data

(60) Continuation of application No. 09/963,018, filed on Sep. 25, 2001, now Pat. No. 6,511,992, which is a division of application No. 09/564,527, filed on May 4, 2000, now Pat. No. 6,323,220.

(30) Foreign Application Priority Data

May 5, 1999 (FR) .............................. 99.05690

(51) Int. Cl.$^7$ ...................... A61K 31/445; A61K 31/44; C07D 413/02; C07D 213/02
(52) U.S. Cl. ...................... 514/317; 514/336; 514/326; 546/194; 546/207; 544/111
(58) Field of Search ................. 546/194, 207; 514/317, 326, 336; 544/111

(56) References Cited

U.S. PATENT DOCUMENTS 6,015,824 A * 1/2000 Alanine et al. ............. 514/375

OTHER PUBLICATIONS

Chiral Separation of Iobeline . . . McCurdy et al 1999.*
Effect of Stimulation . . . A.V. Terry et al 1996 Psychopharmacology.*
Effect of Lobeline . . . Michael Decker et al 1993.*
Enhancer and Delacour, Behav. Brain. Res., 1988, 31, 47–59.
Lebrun et al., Eur. J. Pharmacol., 2000, 401, 205–212.
Le Moal et al., Dement. Geriatr. Cogn. Disord., 1997, 8, 281–287.
Perlstein et al., Am. J. Psychiatry, 2001, 158, (7), 1105–1113.
Ragland et al., Am. J. Psychiatry, 2001, 158 (7), 1114–1125.
Damaj et al., Journal of Pharmacology and Experimental Therapeutics 282(1):410–419.

* cited by examiner

*Primary Examiner*—Rita Desai
(74) *Attorney, Agent, or Firm*—The Firm of Hueschen and Sage

(57) ABSTRACT

The invention relates to a compound of formula (I):

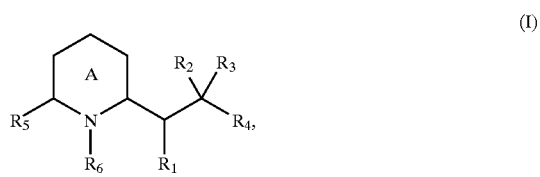

wherein:

A represents pyridine, pyridinium or piperidine $R_1$, $R_2$, $R_3$ and $R_4$ are as defined in the description $R_5$ represents hydrogen, a nitrogen-containing heterocycle or a group of formula (II):

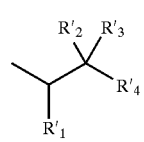

$R_6$ represents hydrogen or linear or branched ($C_1$–$C_6$) alkyl.

and medicinal products containing the same which are useful in treating pain or deficiencies in memory.

3 Claims, No Drawings

SUBSTITUTED PYRIDINE OR PIPERIDINE COMPOUNDS

This application is a continuation of U.S. Pat. Application Ser. No. 09/963,018 filed Sep. 25, 2001 now U.S. Pat. Application No. 6,511,992 which is division of U.S. Ser. No. 09/564,527 filed May 4, 2000 now U.S. Pat. No. 6,323,220.

FIELD OF THE INVENTION

The present invention relates to new substituted pyridine or piperidine compounds and to their use as facilitators of memory and cognition and as antalgic agents.

BACKGROUND OF THE INVENTION

Ageing of the population due to increased life expectancy has brought with it a major increase in cognitive disorders associated with normal cerebral ageing and with pathological cerebral ageing occurring in the course of neurodegenerative diseases such as, for example, Alzheimer's disease.

The majority of substances used today in treating cognitive disorders associated with ageing act by facilitating the central cholinergic systems—either directly, as in the case of acetylcholinesterase inhibitors (tacrine donepezil) and cholinergic agonists (nefiracetam), or indirectly, as in the case of nootropic agents (piracetam, pramiracetam) and cerebral vasodilators (vinpocetine).

Besides their cognitive properties, substances acting directly on the central cholinergic systems often have antalgic properties but also have hypothermic properties, which can be undesirable.

It has been therefore been especially valuable to synthesise new compounds that are capable of opposing the cognitive disorders associated with ageing and/or of improving cognitive processes and that can possess antalgic properties without having hypothermic activity.

DESCRIPTION OF THE PRIOR ART

The literature discloses substituted piperidine compounds which are described as products of synthesis and/or of alkaloids (J. Chem. Soc., Perkin Trans. 1, 1991, (3), pp. 611–616; Heterocycles, 1985, 23 (4), pp. 831–834; Can. J. Chem., 1996, 74 (12), pp. 2444–2453).

Substituted pyridine compounds have also been described with reference to their synthesis (J. Chem. Soc., Dalton Trans., 1998, (6), pp. 917–922) or their interactions in metal complexes (J. Chem. Soc., Chem. Commun., 1987, (19), pp. 1457–1459; J. Am. Chem. Soc., 1985, 107 (4), pp. 917–925).

The compounds of the present invention are new and have properties that, from a pharmacological point of view, are especially valuable.

DETAILED DESCRIPTION OF THE INVENTION

More specifically, the present invention relates to compounds of formula (I):

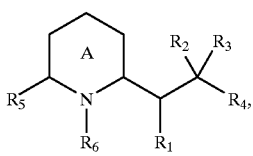

(I)

wherein:

♦ A represents a pyridine, pyridinium or piperidine group,

♦ $R_2$ represents a hydrogen atom and $R_3$ represents a hydroxy group, or $R_2$ and $R_3$ together form an oxo group, ♦ $R_4$ represents an unsubstituted or substituted phenyl group, an unsubstituted or substituted naphthyl group or an unsubstituted or substituted heteroaryl group, ♦ $R_1$ represents a hydrogen atom, or $R_1$ and $R_4$, together with the two carbon atoms carrying them, form a ring containing 6 carbon atoms, or $R_1$ and $R_2$ form an additional bond and, in that case, $R_3$ represents a 5- or 6-membered heterocycle that contains a nitrogen atom by which it is bound and that may contain another hetero atom selected from sulphur, oxygen and nitrogen, ♦ $R_5$ represents:

a 5- or 6-membered heterocycle that contains a nitrogen atom by which it is bonded to the ring A and that may contain another hetero atom selected from sulphur, oxygen and nitrogen, a group of formula (II):

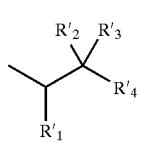

(II)

wherein $R'_1$, $R'_2$, $R'_3$ and $R'_4$ may have the same meanings as $R_1$, $R_2$, $R_3$ and $R_4$, respectively, or a hydrogen atom and, in that case, $R_4$ cannot represent an unsubstituted phenyl group, an unsubstituted naphthyl group or an heteroaryl group, ♦ $R_6$ represents a hydrogen atom or a linear or branched ($C_1$–$C_6$)alkyl group, the group $R_6$ being present or absent depending on the nature of the ring A, heteroaryl being understood to mean any aromatic, mono- or bi-cyclic, 5- to 10-membered group containing from 1 to 3 hetero atoms selected from oxygen, nitrogen and sulphur, the term "substituted" used in respect of the expressions "phenyl", "naphthyl" or "heteroaryl" being understood to mean that the groups concerned may be substituted by one or more groups, which may be the same or different, selected from linear or branched ($C_1$–$C_6$) alkyl, linear or branched ($C_1$–$C_6$)alkoxy, mercapto, linear or branched ($C_1$–$C_6$)-alkylthio, amino, linear or branched ($C_1$–$C_6$)alkylamino, di-($C_1$–$C_6$)alkylamino in which each alkyl moiety is linear or branched, linear or branched ($C_1$–$C_6$)polyhaloalkyl and hydroxy and halogen atoms, it being understood that:

when $R_2$ and $R_3$ together form an oxo group and simultaneously $R_5$ represents a hydrogen atom and $R_6$ represents a hydrogen atom or does not exist, then $R_4$ is other than a phenyl group substituted by one group selected from hydroxy, alkoxy, $CF_3$ and halogen (except for bromine when A represents a piperidine group), or by several groups selected from hydroxy and alkoxy, when R₂ represents a hydrogen atom and R₃ represents a hydroxy group and simultaneously R₅ represents a hydrogen atom and R₆ represents a hydrogen atom or does not exist, then R₄ is other than a phenyl group substituted by one group selected from hydroxy, linear or branched (C₁–C₆)alkoxy, linear or branched (C₁–C₆)alkyl and chlorine, or by several groups selected from hydroxy and alkoxy, the compound of formula (I) may not represent 1-(1,3-benzodioxol-5-yl)-2-(2-pyridinyl)ethanol nor 2-(2-pyridinyl)cyclohexanone, their enantiomers and diastereoisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid etc.

Among the pharmaceutically acceptable bases there may be mentioned, without implying any limitation, sodium hydroxide, potassium hydroxide, triethylamine, tert-butylamine etc.

Preferred compounds of the invention are compounds of formula (I) wherein the group

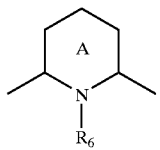

represents a pyridinyl group, an N-methylpyridinium group, a piperidinyl group or an N-methylpiperidinyl group.

Preferred substituents R₄ are a phenyl group or substituted phenyl group, especially substituted by a halogen atom, preferably a bromine atom.

Advantageously, the invention relates to compounds of formula (I) wherein R₅ represents a hydrogen atom or a group of formula (II).

Preferred groups R₂ and R₃ are those wherein R₂ and R₃ together form an oxo group or R₂ represents a hydrogen atom and R₃ represents a hydroxy group.

Even more advantageously, the invention relates to the compounds of formula (I) which are:
1-(4-bromophenyl)-2-(1-methyl-2-piperidinyl)-1-ethanone,
(R)-1-(4-bromophenyl)-2-(1-methyl-2-piperidinyl)-1-ethanone,
(S)-1-(4-bromophenyl)-2-(1-methyl-2-piperidinyl)-1-ethanone,
1-(4-bromophenyl)-2-(1-methyl-2-piperidinyl)-1-ethanol,
(S,S)-1-(4-bromophenyl)-2-(1-methyl-2-piperidinyl)-1-ethanol,
(R,R)-1-(4-bromophenyl)-2-(1-methyl-2-piperidinyl)-1-ethanol,
1-methyl-2-[2-oxo-2-(4-bromophenyl)ethyl]pyridinium iodide.

The enantiomers and diastereoisomers, as well as the addition salts with a pharmaceutically acceptable acid or base, of the preferred compounds of the invention form an integral part of the invention.

The invention relates also to a process for the preparation of compounds of formula (I), which process is characterised in that there is used as starting material the compound of formula (III):

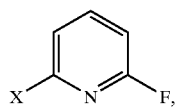

(III)

wherein X represents a hydrogen or fluorine atom, which is alkylated by means of an agent such as, for example, alkyl para-toluenesulphonate or alkyl trifluoromethanesulphonate to yield the compound of formula (IV):

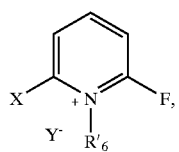

(IV)

wherein X is as defined hereinbefore, R'₆ represents a linear or branched (C₁–C₆)alkyl group and Y⁻ represents a para-toluenesulphonate or trifluoromethanesulphonate group for example, which is reacted with one or two compounds, which may be the same or different, of formula (V)

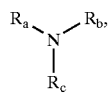

(V)

wherein R$_a$ and R$_b$, together with the nitrogen atom carrying them, form a 5- or 6-membered heterocycle which may contain, in addition to the nitrogen atom, another hetero atom selected from sulphur, oxygen and nitrogen, and R$_c$ represents a hydrogen atom or a group of formula (VI):

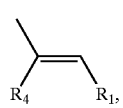

(VI)

wherein R₄ and R₁ are as defined hereinbefore,
it being understood that at least one of the compounds of formula (V) contains a group of formula (VI),
to yield the compound of formula (I/a), a particular case of the compounds of formula (I):

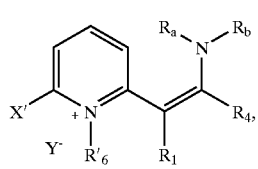

(I/a)

wherein R₁, R₄, R$_a$, R$_b$, R'₆ and Y⁻ are as defined hereinbefore and X' represents a hydrogen atom, a group —NR'$_a$R'$_b$ (wherein R'$_a$ and R'$_b$ may have any of the meanings of $R_a$ and $R_b$, respectively) or a group of formula (VII)

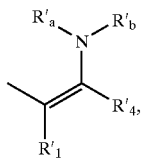
(VII)

wherein $R'_a$, $R'_b$, $R'_1$ and $R'_4$ may have any of the meanings of $R_a$, $R_b$, $R_1$ and $R_4$, respectively, which compound of formula (I/a) may be subjected to halohydric acid such as HCl, HBr or HI, or to the action of ammonium salts such as $NH_4^+PF_6^-$ to yield a compound of formula (I/a'):

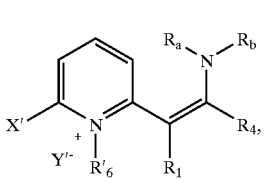
(I/a')

wherein $R_1$, $R_4$, $R_a$, $R_b$, $R'_6$ and $X'$ are as defined hereinbefore and $Y'^-$ represents anion or a $PF_6^-$ group, which compound of formula (I/a') may be hydrolysed using a concentrated hydrochloric acid solution to yield the compound of formula (I/b), a particular case of the compounds of formula (I):

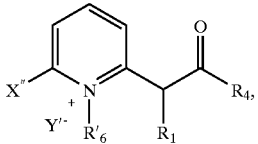
(I/b)

wherein $R_1$, $R_4$, $R'_6$ and $Y'^-$ are as defined hereinbefore and $X''$ represents a hydrogen atom, a group $—NR'_aR'_b$ as defined hereinbefore or a group of formula (VIII):

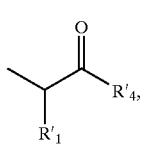
(VIII)

wherein $R'_1$, and $R'_4$ may have any of the meanings of $R_1$ and $R_4$, respectively, the compounds of formula (I/a), (I/a') and (I/b) constituting the compound of formula (I/c) a particular case of the compounds of formula (I):

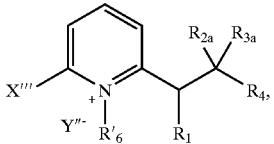
(I/c)

wherein $R_1$, $R_4$ and $R'_6^-$ are as defined hereinbefore, $Y''^-$ represents a group $Y^-$ or $Y'^-$ as defined hereinbefore, $R_{2a}$ and $R_{3a}$ together form an oxo group, or $R_{2a}$ and $R_1$ form an additional bond and, in that case, $R_{3a}$ represents a group $NR'_aR'_b$ as defined hereinbefore, and $X'''$ represents a hydrogen atom, a group $NR'_aR'_b$ or a group of formula (IX):

(IX)

wherein $R'_1$, $R'_{2a}$, $R'_{3a}$ and $R'_4$ may have any of the meanings of $R_1$, $R_{2a}$, $R_{3a}$ and $R_4$, respectively, which is converted into a corresponding iodinated salt by the action of NaI to yield the compound of formula (I/d), a particular case of the compounds of formula (I):

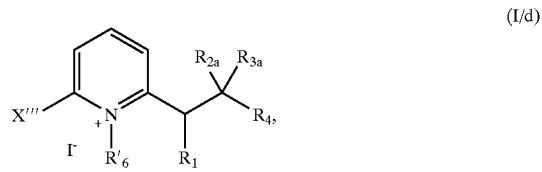
(I/d)

wherein $R_1$, $R_{2a}$, $R_{3a}$, $R_4$, $R'_6$ and $X'''$ are as defined hereinbefore, which is either subjected to catalytic hydrogenation, for example over platinum oxide, to yield the compound of formula (I/e), a particular case of the compounds of formula (I):

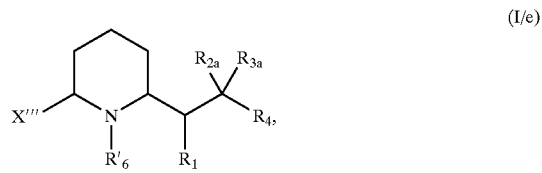
(I/e)

wherein $R_1$, $R_{2a}$, $R_{3a}$, $R_4$, $X'''$ and $R'_6$ are as defined hereinbefore, or subjected to the action of a pyridinium salt to yield the compound of formula (I/f), a particular case of the compounds of formula (I):

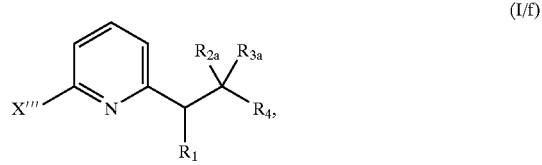
(I/f)

wherein $R_1$, $R_{2a}$, $R_{3a}$, $R_4$ and $X'''$ are as defined hereinbefore, which may be hydrogenated by catalytic hydrogenation to yield the compound of formula (I/g), a particular case of the compounds of formula (I):

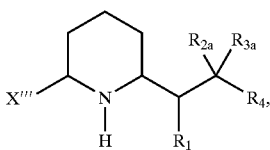

(I/g)

wherein $R_1$, $R_{2a}$, $R_{3a}$, $R_4$ and $X'''$ are as defined hereinbefore, it being possible for the compounds of formulae (I/b) and (I/c) to (I/g) wherein $R_{2a}$ and $R_{3a}$ together form an oxo group to be subjected to the action of a reducing agent such as, for example, $NaBH_4$ to yield the compound of formula (I/h), a particular case of the compounds of formula (I):

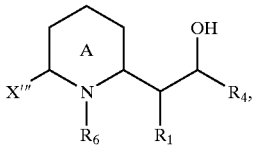

(I/h)

wherein A, $R_1$, $R_4$ and $R_6$ are as defined hereinbefore and $X'''$ represents a hydrogen atom, a group $NR'_aR'_b$ as defined hereinbefore or a group of formula (X):

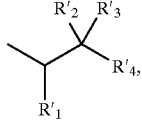

(X)

wherein $R'_1$, $R'_2$, $R'_3$ and $R'_4$ are as defined hereinbefore, which compound of formula (I/h) can be obtained as pure enantiomers from compounds of formula (I/b) and (I/c) to (I/g) wherein $R_{2a}$ and $R_{3a}$ together form an oxo group using an enantioselective reduction catalyst such as (R,R)-(−) or (S,S)-(+)-N,N'-bis(3,5-di-tert-butylsalicylidene-1,2-cyclohexanediaminomanganese (III) chloride, the compounds of formulae (I/a) to (I/h) constituting the totality of the compounds of the invention, which may be purified according to a conventional separation technique, are converted, if desired, into their addition salts with a pharmaceutically acceptable acid or base and are separated, where appropriate, into their isomers according to a conventional separation technique.

In addition to the fact that the compounds of the present invention are new, they exhibit antalgic properties and properties facilitating cognitive processes, rendering them of use in the treatment of pain and of cognitive deficiencies associated with cerebral ageing and with neurodegenerative diseases, such as Alzheimer's disease, Parkinson's disease, Pick's disease, Korsakoff's disease and frontal lobe and subcortical dementias.

The invention relates also to pharmaceutical compositions comprising as active ingredient at least one compound of formula (I) together with one or more appropriate, inert, non-toxic excipients. Among the pharmaceutical compositions according to the invention there may be mentioned more especially those that are suitable for oral, parenteral (intravenous or subcutaneous) and nasal administration, tablets or dragees, sublingual tablets, gelatin capsules, lozenges, suppositories, creams, ointments, dermal gels, injectable preparations, drinkable suspensions etc.

The dosage used can be adapted to the nature and the severity of the disorder, the administration route and the age and weight of the patient. The dosage varies from 0.01 mg to 1 g per day in one or more administrations.

The following Examples illustrate the invention but do not limit it in any way.

The following Preparations yield compounds of the invention or synthesis intermediates that are useful in the preparation of compounds of the invention.

Preparation 1: 2-Fluoro-1-methylpyridinium 4-methylbenzenesulphonate 10 mmol of 2-fluoropyridine and 10 mmol of methyl 4-methylbenzenesulphonate are mixed in a 50 ml round-bottomed flask and stirred for 6 hours at 70° C. under a nitrogen atmosphere. The salt obtained in the form of a white solid is used without additional purification in the following step.

Preparation 2: 1-(1-Phenylvinyl)pyrrolidine 100 g of molecular sieve are heated at 500° C. for 8 hours and then added to a mixture of 20 mmol of acetophenone and 22 mmol of pyrrolidine in 200 ml of anhydrous ether. The reaction mixture is stirred at ambient temperature until, in the infra-red, no more free ketone (C=O 1689 $cm^{-1}$) is detected in the supernatant and the absorption for the enamine (C=C—N 1600 $cm^{-1}$) is at a maximum. The mixture is then filtered and the molecular sieve is washed with ether. The solvent is evaporated off under reduced pressure and the crude residue is purified by distillation under reduced pressure.

Boiling point: 110° C./2 mm Hg

Preparations 3 to 11 are obtained by proceeding as in Preparation 2.

Preparation 3: 4-(1-Phenylvinyl)morpholine
Boiling point: 125° C./2 mm Hg
Preparation 4: 1-[1-(4-Methylphenyl)vinyl]pyrrolidine
Boiling point: 135° C./10 mm Hg
Preparation 5: 1-[1-(4-Methoxyphenyl)vinyl]pyrrolidine
Boiling point: 160° C./0.4 mm Hg
Preparation 6: 1-[1-(4-Chlorophenyl)vinyl]pyrrolidine
Boiling point: 125° C./10 mm Hg
Preparation 7: 1-[1-(4-Bromophenyl)vinyl]pyrrolidine
Boiling point: 160° C./0.3 mm Hg
Preparation 8: 1-[1-(4-Fluorophenyl)vinyl]pyrrolidine
Boiling point: 140° C./0.3 mm Hg
Preparation 9: 1-[1-(2-Bromophenyl)vinyl]pyrrolidine
Boiling point: 130° C./0.3 mm Hg
Preparation 10: 1-[1-(3-Bromophenyl)vinyl]pyrrolidine
Boiling point: 165° C./0.3 mm Hg
Preparation 11: 1-(1-Cyclohexen-1-yl)pyrrolidine 1 g of para-toluenesulphonic acid is added to a mixture of 20 mmol of cyclohexanone and 22 mmol of pyrrolidine in 200 ml of dry benzene. The reaction mixture is stirred at reflux until, in the infra-red, the ketone has disappeared, with the enamine concomitantly appearing. The solvent is then evaporated off and the crude residue is purified by distillation in vacuo.

Boiling point: 110° C./15 mm Hg
Preparation 12: 1-(1-Cyclohexen-1-yl)morpholine

The procedure is as in Preparation 11, the benzene being replaced by toluene and the pyrrolidine by morpholine.

Boiling point: 140° C./15 mm Hg
Preparation 13: 2,6-Difluoro-1-methylpyridinium trifluoromethanesulphonate 10 mmol of 2,6-difluoropyridine and 10 mmol of trifluoromethanesulphonic acid are mixed in a 50 ml round-bottomed flask and the mixture is stirred for 1 hour at ambient temperature under a nitrogen atmosphere. The white solid obtained is used directly in the following reaction without further purification.

Preparation 14: 1-{1-[4-(Dimethylamino)phenyl]vinyl}pyrrolidine

The procedure is as in Preparation 2.

Preparation 15: 1-[1-(2-Fluorophenyl)vinyl]pyrrolidine

The procedure is as in Preparation 2.

Preparation 16: 1-{1-[4-(Methylthio)phenyl]vinyl}pyrrolidine

The procedure is as in Preparation 2.

Preparation 17: 1-{1-[4-(Trifluoromethyl)phenyl]vinyl}pyrrolidine

The procedure is as in Preparation 2.

Preparation 18: 2-Fluoro-1-ethylpyridinium-4-methylbenzenesulfonate

Title product is obtained using the same procedure than in Preparation 1 replacing methyl-4-methylbenzenesulfonate by ethyl-4-methylbenzenesulfonate.

EXAMPLE 1

1-Methyl-2-[2-(4-methylphenyl)-2-oxoethyl]pyridinium hexafluorophosphate 20 mmol of the compound obtained in Preparation 1 are dissolved in 15 ml of anhydrous acetonitrile under a nitrogen atmosphere, and 22 mmol of the compound obtained in Preparation 4, in 10 ml of acetonitrile, are added dropwise at ambient temperature. The reaction mixture is stirred at 80° C. for 2 hours and the solution becomes red. The solvent is evaporated off in vacuo and the viscous red residue is taken up in 30 ml of concentrated hydrochloric acid and heated at reflux for 3 hours. The dark brown solution obtained is cooled to ambient temperature and then 22 mmol of ammonium hexafluorophosphate are added. The precipitate obtained is filtered off, washed with cold water and with ethyl acetate, and then recrystallised from ethanol.

Melting point: 163–165° C.

Elementary microanalysis:

|  | C | H | N |
|---|---|---|---|
| % calculated: | 47.05 | 3.95 | 3.92 |
| % found: | 47.18 | 3.88 | 3.81 |

EXAMPLE 2

1-Methyl-2-[2-(4-methylphenyl)-2-oxoethyl]pyridinium Iodide 10 mmol of the compound obtained in Example 1 are dissolved in 35 ml of acetone, and 15 mmol of NaI are added in portions of 100 mg. A white precipitate is obtained immediately and the mixture is stirred for 14 hours in a sealed tube at ambient temperature. The white solid obtained is filtered off and washed with acetone.

Melting point: 191–193° C.

Elementary microanalysis:

|  | C | H | N |
|---|---|---|---|
| % calculated: | 49.56 | 4.16 | 4.13 |
| % found: | 49.82 | 4.12 | 4.40 |

The procedure in Examples 3 to 14 is as in Examples 1 and 2.

EXAMPLE 3

1-Methyl-2-(2-oxo-2-(4-methoxyphenyl)ethyl)pyridinium hexafluorophosphate

Starting compounds: Preparations 1 and 5

Melting point: 168–170° C.

Elementary microanalysis:

|  | C | H | N |
|---|---|---|---|
| % calculated: | 46.50 | 4.17 | 3.62 |
| % found: | 46.82 | 4.10 | 3.78 |

EXAMPLE 4

1-Methyl-2-[2-oxo-2-(4-methoxyphenyl)ethyl]pyridinium iodide

Starting compound: Example 3

Melting point: 214–216° C.

Elementary microanalysis:

|  | C | H | N |
|---|---|---|---|
| % calculated: | 47.78 | 4.37 | 3.79 |
| % found: | 48.67 | 4.68 | 4.02 |

EXAMPLE 5

1-Methyl-2-[2-oxo-2-(4-chlorophenyl)ethyl]pyridinium hexafluorophosphate

Starting compounds: Preparations 1 and 6

Melting point: 152–154° C.

Elementary microanalysis:

|  | C | H | N |
|---|---|---|---|
| % calculated: | 42.96 | 3.35 | 3.58 |
| % found: | 42.80 | 3.20 | 3.18 |

EXAMPLE 6

1-Methyl-2-[2-oxo-2-(4-chlorophenyl)ethyl]pyridinium iodide

Starting compound: Example 5

Melting point: 212–214° C.

Elementary microanalysis:

|  | C | H | N |
|---|---|---|---|
| % calculated: | 45.04 | 3.51 | 3.75 |
| % found: | 45.50 | 3.65 | 3.88 |

EXAMPLE 7

1-Methyl-2-[2-oxo-2-(4-bromophenyl)ethyl]
pyridinium hexafluorophosphate

Starting compounds: Preparations 1 and 7
Melting point: 185–187° C.
Elementary microanalysis:

|  | C | H | N |
|---|---|---|---|
| % calculated: | 38.62 | 3.01 | 3.22 |
| % found: | 38.43 | 3.10 | 3.54 |

EXAMPLE 8

1-Methyl-2-[2-oxo-2-(4-bromophenyl)ethyl]
pyridinium iodide

Starting compound: Example 7
Melting point: 222–224° C.
Elementary microanalysis:

|  | C | H | N |
|---|---|---|---|
| % calculated: | 40.30 | 3.14 | 3.36 |
| % found: | 40.46 | 3.30 | 3.26 |

EXAMPLE 9

1-Methyl-2-(2-oxocyclohexyl)pyridinium
hexafluorophosphate

Starting compounds: Preparations 1 and 11 or 12
Elementary microanalysis:

|  | C | H | N |
|---|---|---|---|
| % calculated: | 42.97 | 4.81 | 4.18 |
| % found: | 43.21 | 4.76 | 4.01 |

EXAMPLE 10

1-Methyl-2-(2-oxocyclohexyl)pyridinium iodide

Starting compound: Example 9
Melting point: 151–153° C.
Elementary microanalysis:

|  | C | H | N |
|---|---|---|---|
| % calculated: | 45.42 | 5.09 | 4.42 |
| % found: | 45.76 | 4.96 | 4.66 |

EXAMPLE 11

1-Methyl-2-[2-oxo-2-(3-bromophenyl)ethyl]
pyridinium hexafluorophosphate

Starting compounds: Preparations 1 and 10

EXAMPLE 12

1-Methyl-2-[2-oxo-2-(3-bromophenyl)ethyl]
pyridinium iodide

Starting compound: Example 11
Melting point: 217–218° C.
Elementary microanalysis:

|  | C | H | N |
|---|---|---|---|
| % calculated: | 40.30 | 3.14 | 3.36 |
| % found: | 40.20 | 3.25 | 2.90 |

EXAMPLE 13

1-Methyl-2-[2-oxo-2-(2-bromophenyl)ethyl]
pyridinium hexafluorophosphate

Starting compounds: Preparations 1 and 9

EXAMPLE 14

1-Methyl-2-[2-oxo-2-(2-bromophenyl)ethyl]
pyridinium iodide

Starting compound: Example 13
Melting point: 204–205° C.
Elementary microanalysis:

|  | C | H | N |
|---|---|---|---|
| % calculated: | 40.30 | 3.14 | 3.36 |
| % found: | 40.26 | 3.32 | 3.04 |

EXAMPLE 15a

1-Methyl-2-[2-oxo-(2-fluorophenyl)ethyl]pyridinium
iodide

The procedure is as in Examples 1 and 2, starting from the compound obtained in Preparation 15.

EXAMPLE 15b 1-(2-Fluorophenyl)-2-(1-methyl-2-piperidinyl)
ethanone hydriodide 3 mmol of the compound obtained in Example 15a are dissolved in 150 ml of ethanol, and 50 mg of platinum oxide are added all at once. Hydrogenation is carried out at an initial pressure of 5 atm at 24° C. When the calculated theoretical volume of hydrogen has been absorbed (after approximately 3 hours), the catalyst is filtered off and washed with ethanol. The solvent is evaporated off and the residue obtained is recrystallised.

Melting point: 118–119° C.

Examples 16 to 21 are obtained by proceeding as in Example 15b.

EXAMPLE 16

2-(1-Methyl-2-piperidinyl)-1-(4-methoxyphenyl)-1-ethanone hydriodide

Starting compound: Example 4
Melting point: 201–203° C.
Elementary microanalysis:

|  | C | H | N |
|---|---|---|---|
| % calculated: | 47.99 | 5.91 | 3.73 |
| % found: | 48.10 | 6.01 | 3.45 |

EXAMPLE 17

2-(1-Methyl-2-piperidinyl)-1-(4-chlorophenyl)-1-ethanone hydriodide

Starting compound: Example 6
Melting point: 158–160° C.
Elementary microanalysis:

|  | C | H | N |
|---|---|---|---|
| % calculated: | 44.32 | 5.05 | 3.69 |
| % found: | 44.46 | 5.32 | 3.68 |

EXAMPLE 18

2-(1-Methyl-2-piperidinyl)-1-(4-bromophenyl)-1-ethanone hydriodide

Starting compound: Example 8
Melting point: 182–184° C.
Elementary microanalysis:

|  | C | H | N |
|---|---|---|---|
| % calculated: | 39.72 | 4.53 | 3.31 |
| % found: | 39.81 | 4.60 | 3.54 |

EXAMPLE 18a (R)-2-(1-Methyl-2-piperidinyl)-1-(4-bromophenyl)-1-ethanone hydrochloride A solution of oxalyl chloride (5 mmol) in dry $CH_2Cl_2$ (10 ml) was placed in an oven-dried 25 ml flask which was degassed and filled with nitrogen. DMSO (10 mmol) was added dropwise through a syringe at −50 to −60° C. The reaction mixture was stirred for 5 minutes. A solution of compound of Example 60 (2) (0,5 mmol) in $CH_2Cl_2$ (5 ml) was then added dropwise within 5 minutes and stirring was continued for another 30 minutes. Triethylamine (30 mmol) was added and the solution was stirred for 10 minutes and then allowed to warm to room temperature. Water was then added to the reaction mixture and the aqueous solution was extracted with $CH_2Cl_2$. The combined organic phases was dried ($MgSO_4$) and concentrated. The residue was purified by flash column chromatography (silica gel, AcOEt-MeOH—$NH_4OH$) affording an unstable light yellow oil which was immediately dissolved in an HCl-ether solution forming a white solid. Recrystallisation of this solid from MeOH-ether produced pure title product.

Melting point: 191–194° C.
$[\alpha]=+10$ (c=0.1; MeOH)

EXAMPLE 18b (S)-2-(1-Methyl-2-piperidinyl)-1-(4-bromophenyl)-1-ethanone hydrochloride The title product is obtained using the same procedure than in Example 18a starting from compound of Example 60 (1).

Melting point. 192–194° C.
$[\alpha]=-9$ (c=0.1; MeOH)

EXAMPLE 19

2-(1-Methyl-2-piperidinyl)cyclohexanone hydriodide

Starting compound: Example 10
Melting point: 160–162° C.

EXAMPLE 20

2-(1-Methyl-2-piperidinyl)-1-(3-bromophenyl)-1-ethanone hydriodide

Starting compound: Example 12
Melting point: 134–136° C.
Elementary microanalysis:

|  | C | H | N |
|---|---|---|---|
| % calculated: | 39.72 | 4.53 | 3.31 |
| % found: | 39.88 | 4.45 | 3.26 |

EXAMPLE 21

2-(1-Methyl-2-piperidinyl)-1-(2-bromophenyl)-1-ethanone hydriodide

Starting compound: Example 14
Melting point: 163.5–164° C.
Elementary microanalysis:

|  | C | H | N |
|---|---|---|---|
| % calculated: | 39.72 | 4.53 | 3.31 |
| % found: | 39.66 | 4.47 | 3.26 |

EXAMPLE 22

1-Methyl-2-[2-phenyl-2-(1-pyrrolidinyl)ethenyl]pyridinium hexafluorophosphate 20 mmol of the compound obtained in Preparation 1 are dissolved in 15 ml of dry acetonitrile under a nitrogen atmosphere. A solution of 22 mmol of the compound obtained in Preparation 2 in 10 ml of acetonitrile is added dropwise, with stirring, at ambient temperature. The reaction mixture is stirred for 14 hours at ambient temperature and then for 2 hours at 80° C. The solution becomes red. The solvent is evaporated off under reduced pressure, and 30 ml of cold water and then 22 mmol of ammonium hexafluorophosphate in 20 ml of ethyl acetate/ether (1/1) are added to the viscous red residue obtained. After filtration and washing with water and then with AcOEt/Et$_2$O (1/1), the pure title product is obtained.

Melting point: 143–145° C.

Elementary microanalysis:

|  | C | H | N |
|---|---|---|---|
| % calculated: | 52.67 | 5.16 | 7.83 |
| % found: | 52.97 | 5.26 | 7.81 |

EXAMPLE 23

1-Methyl-2-[2-phenyl-2-(1-pyrrolidinyl)ethenyl]pyridinium iodide

The same procedure is used as in Example 2.

Melting point: 200–202° C.

EXAMPLE 24

1-Methyl-2-[2-(4-morpholinyl)-2-phenylethenyl]pyridinium hexafluorophosphate

The same procedure is used as in Example 22.

Starting compounds: Preparations 1 and 3

Melting point:. 168–170° C.

Elementary microanalysis:

|  | C | H | N |
|---|---|---|---|
| % calculated: | 50.71 | 4.96 | 6.57 |
| % found: | 50.68 | 4.88 | 6.44 |

EXAMPLE 25

1-Methyl-2-[2-(4-morpholinyl)-2-phenylethenyl]pyridinium iodide

The procedure is as in Example 2.

EXAMPLE 26

1-Methyl-2-(4-morpholinyl)-6-[2-(4-morpholinyl)-2-phenylethenyl]-pyridinium hexafluorophosphate 20 mmol of the compound obtained in Preparation 13 are dissolved in 15 ml of dry acetonitrile under a nitrogen atmosphere. 22 mmol of morpholine and 22 mmol of the compound obtained in Preparation 3 are added and the mixture is stirred for 14 hours at ambient temperature and then for 2 hours at 80° C. The procedure is then as in Example 22.

EXAMPLE 27

1-Methyl-2-(4-morpholinyl)-6-[2-(4-morpholinyl)-2-phenylethenyl]-pyridinium iodide The procedure is as in Example 2.

Melting point: 214–216° C.

EXAMPLE 28

1-Methyl-2,6-bis(2-oxo-2-phenylethyl)pyridinium trifluoromethanesulphonate 20 mmol of the compound obtained in Preparation 13 are dissolved in 15 ml of dry acetonitrile. A solution, in 15 ml of acetonitrile, of 44 mmol of the compound obtained in Preparation 2 is added dropwise at 0° C., with stirring, under a nitrogen atmosphere. The reaction mixture is then stirred for 14 hours at ambient temperature. The solution becomes red; the solvent is then evaporated off and the viscous red residue obtained is taken up in 50 ml of concentrated hydrochloric acid and heated at reflux for 3 hours. After cooling to ambient temperature, the title compound crystallises out in the form of white needles, which are filtered off and then washed with cold water and with ethyl acetate.

Melting point: 175° C.

Elementary microanalysis:

|  | C | H | N |
|---|---|---|---|
| % calculated: | 57.61 | 4.61 | 2.92 |
| % found: | 57.82 | 4.40 | 2.99 |

EXAMPLE 29

1-Methyl-2,6-bis(2-oxo-2-phenylethyl)pyridinium iodide

The procedure is as in Example 2.

Melting point: 197–199° C.

Elementary microanalysis:

|  | C | H | N |
|---|---|---|---|
| % calculated: | 57.76 | 4.41 | 3.06 |
| % found: | 57.88 | 4.52 | 3.35 |

EXAMPLE 30

2,6-Bis[2-(4-bromophenyl)-2-oxoethyl]-1-methylpyridinium trifluoromethanesulphonate The procedure is as in Example 28.

Starting compounds: Preparations 13 and 7

EXAMPLE 31

2,6-Bis[2-(4-bromophenyl)-2-oxoethyl]-1-methylpyridinium iodide

The procedure is as in Example 2.

EXAMPLE 32

1-Methyl-2,6-bis(2-oxocyclohexyl)pyridinium hexafluorophosphate 20 mmol of the compound obtained in Preparation 13 are dissolved in 15 ml of acetonitrile, and 44 mmol of the compound obtained in Preparation 11, dissolved in 15 ml of acetone, are added at 0° C. under a nitrogen atmosphere. The reaction mixture is returned to ambient temperature and stirred for 3 hours at 80° C. The solution becomes red and, after the solvent has been evaporated off under reduced pressure, the residue is taken up in 50 ml of concentrated hydrochloric acid and heated at reflux for 3 hours. After cooling, the solution is filtered to remove any solid impurities and 22 mmol of $NH_4PF_6$ are added. After extraction with ethyl acetate and drying over $MgSO_4$, the solvent is evaporated off under reduced pressure and the solid obtained is recrystallised from an ethanol/ethyl acetate mixture.

Elementary microanalysis:

|              | C     | H    | N    |
|--------------|-------|------|------|
| % calculated: | 50.10 | 5.61 | 3.25 |
| % found:      | 50.28 | 5.31 | 3.66 |

EXAMPLE 33
1-Methyl-2,6-bis(2-oxocyclohexyl)pyridinium iodide

The procedure is as in Example 2.

EXAMPLE 34
1-Methyl-2-[2-(4-methylphenyl)-2-oxoethyl]-6-(2-oxo-2-phenylethyl)-pyridinium trifluoromethanesulphonate 20 mmol of the compound obtained in Preparation 13 are dissolved in 15 ml of dry acetonitrile, and then 22 mmol of the compound obtained in Preparation 2, in 10 ml of acetonitrile, are added dropwise at 0° C. under a nitrogen atmosphere. The reaction mixture is then returned to ambient temperature and stirred for 3 hours at that temperature. 22 mmol of the compound obtained in Preparation 4, in 10 ml of acetonitrile, are then added and the reaction mixture is stirred for a further 14 hours. The solvent is then evaporated off and the viscous red residue obtained is taken up in 50 ml of concentrated hydrochloric acid and heated at reflux for 3 hours. After cooling, the title compound crystallises out in the form of white needles, which are filtered off and washed in succession with water and ethyl acetate.

Melting point: 188–190° C.

Elementary microanalysis:

|              | C     | H    | N    |
|--------------|-------|------|------|
| % calculated: | 58.40 | 4.50 | 2.84 |
| % found:      | 58.54 | 4.76 | 2.78 |

EXAMPLE 35
1-Methyl-2-[2-(4-methylphenyl)-2-oxoethyl]-6-(2-oxo-2-phenylethyl)-pyridinium iodide The procedure is as in Example 2.
Melting point: 205–206° C.
Elementary microanalysis:

|              | C     | H    | N    |
|--------------|-------|------|------|
| % calculated: | 58.59 | 4.71 | 2.91 |
| % found:      | 58.65 | 4.65 | 2.76 |

Examples 36 to 49 are obtained by proceeding as in Examples 34 and 35.

EXAMPLE 36
2-[2-(4-Chlorophenyl)-2-oxoethyl]-1-methyl-6-(2-oxo-2-phenylethyl)-pyridinium trifluoromethanesulphonate Starting compounds: Preparations 13, 2 and 6
Melting point: 199–201° C.

EXAMPLE 37
2-[2-(4-Chlorophenyl)-2-oxoethyl]-1-methyl-6-(2-oxo-2-phenylethyl)-pyridinium iodide Starting compound Example 36
Melting point: 213–215° C.

EXAMPLE 38
2-[2-(4-Fluorophenyl)-2-oxoethyl]-1-methyl-6-(2-oxo-2-phenylethyl)-pyridinium trifluoromethanesulphonate Starting compounds Preparations 13, 2 and 8

EXAMPLE 39
2-[2-(4-Fluorophenyl)-2-oxoethyl]-1-methyl-6-(2-oxo-2-phenylethyl)-pyridinium iodide Starting compound Example 38
Melting point: 220–222° C.

EXAMPLE 40
2-[2-(4-Bromophenyl)-2-oxoethyl]-1-methyl-6-(2-oxo-2-phenylethyl)-pyridinium trifluoromethanesulphonate Starting compounds: Preparations 13, 2 and 7

EXAMPLE 41
2-[2-(4-Bromophenyl)-2-oxoethyl]-1-methyl-6-(2-oxo-2-phenylethyl)-pyridinium iodide Starting compound: Example 40
Melting point: 218–220° C.

EXAMPLE 42
2-[2-(4-Bromophenyl)-2-oxoethyl]-6-[2-(4-chlorophenyl)-2-oxoethyl]-1-methylpyridinium trifluoromethanesulphonate Starting compounds Preparations 13, 6 and 7
Melting point: 226–228° C.

EXAMPLE 43
2-[2-(4-Bromophenyl)-2-oxoethyl]-6-[2-(4-chlorophenyl)-2-oxoethyl]-1-methylpyridinium iodide Starting compound: Example 42
Melting point: 226–227° C.

EXAMPLE 44
2-[2-(4-Methoxyphenyl)-2-oxoethyl]-1-methyl-6-(2-oxo-2-phenylethyl)-pyridinium trifluoromethanesulphonate Starting compounds: Preparations 13, 2 and 5
Melting point: 193–195° C.

EXAMPLE 45
2-[2-(4-Methoxyphenyl)-2-oxoethyl]-1-methyl-6-(2-oxo-2-phenylethyl)-pyridinium iodide Starting compound: Example 44
Melting point: 203–205° C.

EXAMPLE 46

2-[2-(4-Fluorophenyl)-2-oxoethyl]-6-[2-(4-methoxyphenyl)-2-oxoethyl]-1-methylpyridinium trifluoromethanesulphonate Starting compounds: Preparations 13, 5 and 8
Melting point: 208–210° C.

Example 47

2-[2-(4-Fluorophenyl)-2-oxoethyl]-6-[2-(4-methoxyphenyl)-2-oxoethyl]-1-methylpyridinium iodide Starting compound: Example 46
Melting point: 219–220° C.

EXAMPLE 48

2-[2-(4-Methoxyphenyl)-2-oxoethyl]-1-methyl-6-[2-(4-methylphenyl)-2-oxoethyl]pyridinium trifluoromethanesulphonate Starting compounds: Preparations 13, 4 and 5

EXAMPLE 49

2-[2-(4-Methoxyphenyl)-2-oxoethyl]-1-methyl-6-[2-(4-methylphenyl)-2-oxoethyl]pyridinium iodide Starting compound: Example 48

EXAMPLE 50

1-(4-Methoxyphenyl)-2-{1-methyl-6-[2-(4-methylphenyl)-2-oxoethyl]-2-piperidinyl}-1-ethanone hydriodide 3 mmol of the compound obtained in Example 49 are dissolved in 150 ml of ethanol and then 70 mg of platinum oxide are added all at once. Hydrogenation is carried out using an initial pressure of 3 atmospheres at 24° C. when the theoretical volume of hydrogen has been absorbed (after approximately 3 hours), the catalyst is filtered off and washed with ethanol. The solvent is then evaporated off and the title product is obtained in the form of a white solid.

Examples 51 to 56 are obtained by proceeding as in Example 50.

EXAMPLE 51

2-{1-Methyl-6-[2-(4-methylphenyl)-2-oxoethyl]-2-piperidinyl}-1-phenyl-1-ethanone hydriodide Starting compound: Example 35
Melting point: 192–193° C.

EXAMPLE 52

1-(4-Chlorophenyl)-2-[1-methyl-6-(2-oxo-2-phenylethyl)-2-piperidinyl]-1-ethanone hydriodide Starting compound: Example 37
Melting point: 152–154° C.

EXAMPLE 53

1-(4-Fluorophenyl)-2-[1-methyl-6-(2-oxo-2-phenylethyl)-2-piperidinyl]-1-ethanone hydriodide Starting compound: Example 39
Melting point: 152–154° C.

EXAMPLE 54

1-(4-Bromophenyl)-2-{6-[2-(4-chlorophenyl)-2-oxoethyl]-1-methyl-2-piperidinyl}-1-ethanone hydriodide Starting compound: Example 43
Melting point: 200–202° C.

EXAMPLE 55

1-(4-Bromophenyl)-2-[1-methyl-6-(2-oxo-2-phenylethyl)-2-piperidinyl]-1-ethanone hydriodide Starting compound: Example 41

EXAMPLE 56

1-(4-Bromophenyl)-2-{6-[2-(4-bromophenyl)-2-oxoethyl]-1-methyl-2-piperidinyl}-1-ethanone hydriodide Starting compound: Example 31

EXAMPLE 57a

2-{2-[4-(Dimethylamino)phenyl]-2-oxoethyl}-1-methylpyridinium iodide

The procedure is as in Examples 1 and 2, starting from the compound obtained in Preparation 14.

EXAMPLE 57b

1-[4-(Dimethylamino)phenyl]-2-(2-pyridinyl) ethanone 8 mmol of the compound obtained in Example 57a are added to 15 g of boiling pyridine hydrochloride and the dark solution obtained is heated at reflux for 10 minutes. The hot reaction mixture is poured onto 30 g of ice and 20 ml of ammonium hydroxide 37%. After cooling in an ice bath for approximately 2 hours, the title compound crystallises out and the crystals are filtered off and washed with cold water.

EXAMPLE 58

1-(4-Bromophenyl)-2-(2-pyridinyl)-1-ethanol

Step A: 1-(4-Bromophenyl)-2-(2-pyridinyl)-1-ethanone 8 mmol of the compound obtained in Example 8 are added to 15 g of boiling pyridine hydrochloride and the dark solution obtained is heated at reflux for 10 minutes. The hot reaction mixture is poured onto 30 g of ice and 20 ml of ammonium hydroxide 37%. After cooling in an ice bath for approximately 2 hours, the title compound crystallises out in the form of yellow-green crystals, which are filtered off and washed with cold water.

Step B: 1-(4-Bromophenyl)-2-(2-pyridinyl)-1-ethanol 1 mmol of the compound obtained in Step A is dissolved in 15 ml of ethanol, and 1.5 mmol of $NaBH_4$ are added in two portions. The reaction mixture is stirred for 3 hours; the reaction is then quenched using 0.5 ml of acetic acid; the mixture is rendered basic with 10% NaOH, and extracted with dichloromethane (3×15 ml). The organic phase is dried over $MgSO_4$, evaporated and the solid obtained is recrystallised from ethanol.

EXAMPLE 58a

S-(−)-1-(4-Bromophenyl)-2-(2-pyridinyl)-1-ethanol

A solution of $NaBH_4$ (1,51 g, 40 mmol) modified with ethanol (2.34 ml) and tetrahydrofurfuryl alcohol (20 ml) in CHCl₃ (40 ml) was added dropwise to a solution of the compound obtained in step A of Example 58 (8.28 g, 30 mmol) and (R,R)-(−)-Jacobsen's MnCl catalyst (420 mg) in CHCl₃ (30 ml) at −20° C. under a nitrogen atmosphere. The reaction was monitored by TLC and quenched by addition of sat. NH₄Cl solution (15 ml) on completion. The aqueous solution was extracted with CH₂Cl₂ and the extract dried and evaporated. The residue was purified by column chromatography (silica gel, ethyl acetate-petroleum ether) to afford title product.

Melting point: 161–162° C.

$[\alpha]=-34$ (c=1, CHCl₃)

Elementary microanalysis:

|  | C | H | N |
|---|---|---|---|
| % calculated: | 56.14 | 4.35 | 5.04 |
| % found: | 56.25 | 4.06 | 4.99 |

EXAMPLE 58b

R-(+)-1-(4-Bromophenyl)-2-(2-pyridinyl)-1-ethanol

Title product is obtained using the same process than in Example 58a with (S,S)-(+)-Jacobsen's MnCl catalyst.

Melting point: 161–162.5° C.

$[\alpha]=+34$ (c=1, CHCl₃)

Elementary microanalysis:

|  | C | H | N |
|---|---|---|---|
| % calculated: | 56.14 | 4.35 | 5.04 |
| % found. | 56.25 | 4.06 | 4.99 |

EXAMPLE 59

1-(4-Bromophenyl)-2-(2-piperidinyl)-1-ethanol 1 mmol of the compound obtained in Example 58 is dissolved in 20 ml of acetic acid, and 8 mg of platinum oxide are added. The hydrogenation is carried out starting from an initial pressure of 3 atmospheres at 24° C. After reacting for 3 hours, the catalyst is filtered off and washed with dichloromethane. The solvents are evaporated off and the residue obtained is dissolved in 10% sodium hydroxide solution and extracted with dichloromethane. The organic phase is washed with water, dried over MgSO₄ and then evaporated off to yield the title compound in the form of a white solid.

EXAMPLE 60

1-(4-Bromophenyl)-2-(1-methyl-2-piperidinyl)-1-ethanol

The procedure is as in Step B of Example 58, starting from the compound obtained in Example 18.

EXAMPLE 60 (1)

(S,S)-(−)-1-(4-Bromophenyl)-2-(1-methyl-2-piperidinyl)-1-ethanol

To compound obtained in Example 58a (1 mmol) in acetic acid (20 ml) was added platinum oxide (20 mg) and the solution hydrogenated at 5 atm. and 20° C. Removal of the catalyst and then the solvent, followed by addition of dichloromethane and aqueous sodium carbonate, washing and drying of the organic layer, followed by evaporation, gave a mixture of two diastereoisomers of (S,S)-(−)-4'-bromo-norsedamine and (R,S)-(−)-4'-bromo-norallosedamine. Recrystallisation from ethyl acetate/petroleum ether (1:1) gave the pure S,S-isomer of 1-(4-bromophenyl)-2-(2-piperidinyl)ethanol which was dissolved in acetonitrile (25 ml) and aqueous formaldehyde (37%, 25 ml). Then sodium cyanoborohydride (0.312 g, 5 mmol) was added. The mixture was stirred at ambient for 1 hour and acetic acid added. After 20 minutes the solution was neutralised with aqueous sodium hydroxide, extracted with dichloromethane, the extract dried and evaporated and the residue purified by silica gel chromatography to give the title product (recrystallised from ethyl acetate-petroleum ether 1:1).

Melting point: 102–104° C.

$[\alpha]=-28$ (c=1, EtOH)

Elementary microanalysis:

|  | C | H | N |
|---|---|---|---|
| % calculated: | 56.38 | 6.76 | 4.70 |
| % found: | 56.72 | 6.66 | 5.01 |

EXAMPLE 60 (2)

(R,R)-(+)-1-(4-Bromophenyl)-2-(1-methyl-2-piperidinyl)-1-ethanol

Title product is obtained using the same procedure than in Example 60 (1) starting from compound obtained in Example 58b.

Melting point: 102–104° C.

$[\alpha]=+28$ (c=1, EtOH)

Elementary microanalysis:

|  | C | H | N |
|---|---|---|---|
| % calculated: | 56.38 | 6.76 | 4.70 |
| % found: | 56.81 | 6.82 | 4.76 |

EXAMPLE 61a

2-{2-[4-(Methylthio)phenyl]-2-oxoethyl}-1-methylpyridinium iodide

The procedure is as in Examples 1 and 2, starting from the compound obtained in Preparation 16.

EXAMPLE 61b

1-[4-(Methylthio)phenyl]-2-(2-pyridinyl)ethanone

The procedure is as in Example 57b, starting from the compound obtained in Example 61a.

Melting point: 118–119.5° C.

EXAMPLE 62

1-Methyl-2-[2-(4-chlorophenyl)-2-hydroxyethyl]pyridinium iodide

The procedure is as in Step B of Example 58, starting from the compound obtained in Example 6.

Melting point: 172–173.5° C.

EXAMPLE 63

1-Methyl-2-{2-hydroxy-2-[4-(methylthio)phenyl]
ethyl}pyridinium iodide

The procedure is as in Step B of Example 58, starting from the compound obtained in Example 61 a.

Melting point: 145–148° C.

EXAMPLE 64

2-{2-[4-(Dimethylamino)phenyl]-2-
hydroxyethyl}pyridinium iodide

The procedure is as in Step B of Example 58, starting from the compound obtained in Example 57a.

EXAMPLE 65

1-[4-(Methylthio)phenyl]-2-(2-pyridinyl)ethanol

The procedure is as in Step B of Example 58, starting from the compound obtained in Example 61b.

EXAMPLE 66a

1-Methyl-2-{2-oxo-2-[4-(trifluoromethyl)phenyl]
ethyl}pyridinium iodide

The procedure is as in Examples 1 and 2, starting from the compound obtained in Preparation 17.

EXAMPLE 66b 2-(2-Pyridinyl)-1-[4-(trifluoromethyl)phenyl]ethanol

Step A: 2-(2-Pyridinyl)-]-[4-(trfiluoromethyl)phenyl]
ethanone

The procedure is as in Example 57b, starting from the compound obtained in Example 66a.

Step B: 2-(2-Pyridinyl)-1-[4-(trifluoromethyl)phenyl]
ethanol

Starting from the compound obtained in Step A, the procedure is as in Step B of Example 58.

Melting point: 156–158° C.

EXAMPLE 67

1-(2-Fluorophenyl)-2-(2-pyridinyl)ethanol

The procedure is as in Example 66b, starting from the compound obtained in Example 15a.

Melting point: 71–73° C.

EXAMPLE 68

1-(3-Bromophenyl)-2-(2-pyridinyl)ethanol

The procedure is as in Example 66b, starting from the compound obtained in Example 12.

Melting point: 82–84° C.

EXAMPLE 69

1-(2-Bromophenyl)-2-(2-pyridinyl)ethanol

The procedure is as in Example 66b, starting from the compound obtained in Example 14. Oil.

EXAMPLE 70

2-(2-Piperidinyl)-1-[4-(trifluoromethyl)phenyl]
ethanol

The procedure is as in Example 59, starting from the compound obtained in Example 66b.

Melting point: 95–98° C.

EXAMPLE 71

1-(4-Chlorophenyl)-2-(1-methyl-2-piperidinyl)
ethanol

The procedure is as in Step B of Example 58, starting from the compound obtained in Example 17.

Melting point: 84–87° C.

EXAMPLE 72

2-(1-Methyl-2-piperidinyl)-1-[4-(trifluoromethyl)
phenyl]ethanol

The procedure is as in Step B of Example 58, starting from the compound obtained in Step A of Example 66b.

EXAMPLE 73

2-[2-(4-Bromophenyl)-2-oxoethyl]-1-
ethylpyridinium chloride

Title product is obtained using the same procedure than in Example 1 starting from Preparations 1 and 7 without addition of ammonium hexafluorophosphate.

Melting point: 112–114° C.

EXAMPLE 74

2-[2-(4-Bromophenyl)-2-hydroxyethyl]-1-
methylpyridinium Chloride

Title product is obtained using the same procedure than in step B of Example 58 starting from the compound of Example 8.

Melting point: 64–65° C.

Pharmacological Study of the Compounds of the Invention

EXAMPLE A

Acute Toxicity Study

The acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

EXAMPLE B

Abdominal Contractions Induced by Phenyl-p-
benzoquinone (PBQ) in the NMRI Mouse Intraperitoneal administration of an alcoholic solution of PBQ causes abdominal cramps in the mouse (SIEGMUND et al., Proc. Soc. Exp. Biol., 1957, 95, 729–731). The cramps are characterised by repeated contractions of the abdominal musculature, accompanied by extension of the hind limbs. Most analgesics antagonise these abdominal cramps (COLLIER et al., Brit. J. Pharmacol. Chem., 1968, 32, 295–310). At t=0 min., the animals are weighed and the compound being studied is administered by the IP route. A group of control animals is given the solvent used for the compound. At t=30 min., an alcoholic solution of PBQ (0.2%) is administered by the IP route in a volume of 0.25 ml/mouse. Immediately after administration of the PBQ, the animals are placed in cylinders of plexiglass (L=19.5 cm; I.D.=5 cm). From t=35 min. to t=45 min., the animals' reaction is observed and the experimenter notes the total number of abdominal cramps per animal. The results are expressed as the percentage inhibition of the number of abdominal cramps measured in the control animals, at the active dose of the compound studied.

The results obtained show a percentage inhibition ranging from 30 to 90% for low active doses, which attests the antalgic properties of the compounds of the invention.

EXAMPLE C

Social Recognition in the Wistar Rat

Initially described in 1982 by THOR and HOLLOWAY, (J. Comp. Physiol., 1982, 96, 1000–1006), the social recognition test has subsequently been proposed by various authors (DANTZER et al., Psychopharmacology, 1987, 91, 363–368; PERIO et al., Psycho-pharmacology, 1989, 97, 262–268) for studying the mnemocognitive effects of new compounds. The test is based on the natural expression of the olfactory memory of the rat and its natural tendency to forget and allows evaluation of memorisation, by recognition of a young congeneric animal, by an adult rat. A young rat (21 days), taken at random, is placed for 5 minutes in the cage housing an adult rat. With the aid of a video device, the experimenter observes the social recognition behaviour of the adult rat and measures its overall duration. The young rat is then removed from the adult rat's cage and is placed in its own cage until the second introduction. The adult rat is given the compound under test and, after 2 hours, is again brought into the presence (5 minutes) of the young rat. The social recognition behaviour is then observed again and its duration measured. The assessment criterion is the difference ($T_2-T_1$), expressed in seconds, between the "recognition" times of the 2 encounters.

The results obtained show a difference ($T_2-T_1$) ranging from −20 s to −45 s for doses ranging from. 0.3 to 3 mg/kg, which shows that the compounds of the invention very greatly enhance memorisation, even at a low dose.

EXAMPLE D

Object Recognition in the Wistar Rat

The object recognition test in the Wistar rat was initially developed by ENNACEUR and DELACOUR (Behav. Brain Res., 1988, 31, 47–59). The test is based on the spontaneous exploratory activity of the animal and has the characteristics of episodic memory in humans. This memory test is sensitive to ageing (SCALI et al., Eur. J. Pharmacol., 1997, 325, 173–180) and to cholinergic dysfunctions (BARTOLINI et al., Pharm. Biochem. Behav. 1996, 53(2), 277–283) and is based on the differences in the exploration of 2 objects of fairly similar shape—one familiar, the other new. Prior to the test, the animals are habituated to the environment (an enclosure without an object). In the course of a first session, the rats are placed (3 minutes) in the enclosure, in which there are 2 identical objects. The duration of exploration is measured for each object. In the course of the second session (3 minutes), 24 hours later, 1 of the 2 objects is replaced by a new object. The duration of exploration is measured for each object. The assessment criterion is the difference, Delta, expressed in seconds, between the exploration times for the new object and for the familiar object in the course of the second session. The control animals, previously treated with the carrier by the IP route 30 minutes before each session, explore the familiar object and the new object in an identical manner, which indicates that the object introduced earlier has been forgotten. Animals treated with a compound that facilitates mnemocognition preferentially explore the new object, which indicates that the object introduced earlier has been remembered.

The results obtained show a difference, Delta, ranging from 5 s to 10 s, for doses ranging from 0.03 to 3 mg/kg, which shows that the compounds of the invention greatly enhance memorisation, even at a very low dose.

EXAMPLE E

Pharmaceutical Composition

Formulation for the preparation of 1000 tablets each comprising 10 mg of active ingredient:

| | |
|---|---|
| 2-(1-Methyl-2-piperidinyl)-1-(4-bromophenyl)-1-ethanone hydriodide (Example 18) | 10 g |
| Hydroxypropyl cellulose | 2 g |
| Wheat starch | 10 g |
| Lactose | 100 g |
| Magnesium stearate | 3 g |
| Talc | 3 g |

We claim:

1. A method for treating a living animal body afflicted with a condition selected from deficiencies in memory associated with cerebral aging and with neurodegenerative diseases comprising the step of administering a compound selected from those of formula (I):

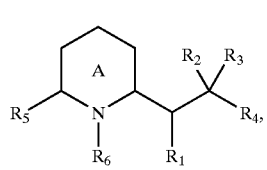

(I)

wherein:
A represents pyridine, pyridinium, or piperidine,
$R_2$ represents hydrogen and $R_3$ represents hydroxy, or $R_2$ and $R_3$ together form oxo,
$R_4$ represents substituted phenyl or substituted naphthyl,
$R_1$ represents hydrogen,
$R_5$ represents a group of formula (II):

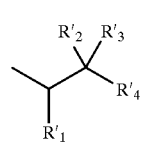

(II)

wherein
$R'_1$ represents hydrogen,
$R'_2$ represents hydrogen and $R'_3$ represents hydroxy, or $R'_2$ and $R'_3$ together form oxo,
$R'_4$ represents unsubstituted or substituted phenyl or unsubstituted or substituted naphthyl,
or $R'_1$ and $R'_4$, together with two carbon atoms carrying them, form a ring containing 6 carbon atoms,
or $R'_1$ and $R'_2$ form an additional bond and, in that case, $R'_3$ represents a 5- or 6-membered heterocycle that contains a nitrogen atom by which it is bound and that may contain another hetero atom selected from sulphur, oxygen, and nitrogen, $R_6$ represents hydrogen or linear or branched ($C_1$–$C_6$) alkyl, the group $R_6$ being present or absent depending on the nature of the ring A, heteroaryl being understood to mean an aromatic, mono- or bicyclic, 5-to 10-membered group containing 1 to 3 hetero atoms selected from oxygen, nitrogen, and sulphur, the term substituted, used with respect to the expressions phenyl, naphthyl, and heteroaryl, being understood to mean that the groups concerned may be substituted by one or more groups, which may be the same or different, selected from linear or branched ($C_1$–$C_6$) alkyl, linear or branched ($C_1$–$C_6$)alkoxy, mercapto, linear or branched ($C_1$–$C_6$)alkylthio, amino, linear or branched ($C_1$–$C_6$)alkylamino, di-($C_1$–$C_6$)alkylamino, in which each alkyl moiety is linear or branched, linear or branched ($C_1$–$C_6$)polyhaloalkyl, hydroxy, and halogen, its enantiomers and diastereoisomers, and addition salts thereof with a pharmaceutically-acceptable acid or base, which compound is effective for alleviation of such condition.

2. The method of claim 1 wherein the compound administered is 2-[2-(4-fluorophenyl)-2-oxoethyl]-6-[2-(4-methoxyphenyl)-2-oxoethyl]-1-methylpyridinium iodide.

3. The method of claim 1 wherein the compound administered is 2-{1-methyl-6-[2-(4-methylphenyl)-2-oxoethyl]-2-piperidinyl}-1-phenyl-1-ethanone hydriodide.

* * * * *